United States Patent [19]

Irwin

[11] Plant 4,390

[45] Mar. 6, 1979

[54] KALANCHOE PLANT

[75] Inventor: Lawrence T. Irwin, Canyon, Tex.

[73] Assignee: J & L Plants, Inc., Canyon, Tex.

[21] Appl. No.: 842,232

[22] Filed: Oct. 14, 1977

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—Frank B. Robb

[57] ABSTRACT

There is disclosed a variety of kalanchoe plant discovered as a sport of a kalanchoe plant known as "Exotic", U.S. Plant Pat. No. 3,149, characterized by the unique orange flower with an unusual and distinctive yellow eye, sturdy upright plant habit, consistent height ranging from 12 to 15 inches, profuse blooms, normally uniform blooming date but ready ability to respond to short day treatment for year around blooming.

2 Drawing Figures

DESCRIPTION OF THE INVENTION

My present invention relates to a new and distinct variety of kalanchoe plant which was discovered by me as a sport of the kalanchoe plant known as "Exotic" U.S. Plant Pat. No. 3,149, this variety having been discovered among a large number of kalanchoe plants which were being grown for commercial production.

I have conducted a breeding program, for many years and in commercial production have kept observing the plants just to seek the possible sports which may have some distinctions and which appear to be susceptible of breeding for the characteristics discovered, and the instant variety is the result of such observation and breeding knowledge as well as the commercial production which we have carried on in greenhouses in Canyon, Tex.

The instant variety is distinguished among others and from the parent variety, and from other varieties of which I am aware as evidenced by the following unique combination of principal characteristics which are outstanding in the new variety and which make it a valuable addition to the various kalanchoe varieties that are presently being produced by me and are commercially available as a result, among these characteristics and the varieties which I have previously developed being the following:

(1) The particularly unique orange flower with an unusual and distinctive yellow eye;

(2) The sturdy, upright plant habit;

(3) Consistent plant height ranging from about 12 inches to 15 inches;

(4) Medium size foliage of an attractive moss green to fern green color;

(5) The profuse blooming habit;

(6) The long lasting qualities as a potted plant;

(7) An ability to initiate and develop flower buds under high night temperatures of summer in contrast to other varieties;

(8) The definite ability to respond to short day treatment in order to produce year arund blooming.

I have caused the plant to be reproduced asexually, by means of cutting in the program of breeding and commercial production which I carry on presently, performed by me in my greenhouse located in Canyon, Tex., this showing that the foregoing characteristics and distinctions come true and established and transmitted through succeeding propagation.

Comparing the features of my new variety of kalanchoe, the particularly distinct aspects reside largely in the unique soft orange flower and very distinctive yellow eye, with somewhat better tendency to break than the parent "Exotic" although it exhibits some of the same vigor and disease resistance that "Exotic" likewise embodies.

In summary it may be stated that on the average the color and peculiarly distinctive yellow eye are the major differences between the parent variety and any other variety with which I am familiar, in the kalanchoe plant art.

In the accompanying drawing I have shown a typical blooming plant of my new variety as well as a close-up view of the flowers as depicted in color as nearly true as it is possible to make the same in a color illustration of this character.

There follows a description of my new variety, with color terminology in accordance with the Munsell Color Cascade published by MacBeth Division of Kollmorgen Corp., except where general color terms which have ordinary dictionary significance are applicable and appropriate, the readings being taken in fiberglass greenhouses.

Parentage: A sport of the variety "Exotic", U.S. Plant Pat. No. 3,149.

Propagation: Holds its distinguishing characteristics through succeeding propagations by cuttings.

Locality where grown and observed: Canyon, Tex.

Plant:

*Form.*—Much branched; upright; compact.

*Growth habit.*—Medium; upright; branching; and compact, usually about 12 to 15 inches in height.

*Rooting.*—Coordinate; roots easily from any part of the stem, roots are numerous and fibrous.

*Blooming habit.*—Compound umbel.

*Blooming season.*—Responds readily to short day treatment; can be brought into bloom the year round by appropriate photoperiod manipulation.

Foliage:

*Size.*—Medium.

*Quantity.*—Abundant.

*Color.*—New foliage — Upper side — 21-15. Under side — 21-14. Old foliage — Upper side — 20-15. Under side — 20-14.

*Texture.*—Upper side — glossy and smooth. Under side — smooth.

*Edge of margin.*—Shape — crenate.

*Disease resistance.* —The new variety is more resistant to root rot than other old varieties and equally as resistant as newer varieties; resistance was determined by side by side comparison in the greenhouse with other varieties.

Flowers:

*Size.*—Flower diameter $\frac{5}{8}''$ — $\frac{3}{4}''$. Flower depth $\frac{3}{4}''$. Petal width about $\frac{1}{4}''$. Length approx. $\frac{3}{8}''$.

*Form.*—Perfect complete ovary superior.

*Color.*—Petals — Upper — deep reddish orange 36-8. Lower — deep reddish orange 36-3. Throat of corolla — light yellowish pink 28-4.

*Blooming period.*—From 4 to 6 weeks.

Fruit: None.

Hardiness: Growing temperature from 45° F. to 100° F. has been experienced in the greenhouse without any problems. The variety is not intended to be winter hardy in temperate climates.

General observations: The new variety produces a very attractive pot plant even with few open flowers. The flowers form a massive flower head composed of hundreds of individual flowers at maturity and retain their fresh appearance during this time. It is notable that while other varieties have a yellow eye, such as the kalanchoe of my breeding and disclosed in U.S. Plant Pat. No. 4,068, the yellow is usually associated with a different flower color, in this instance however my new variety is of an orange, a soft orange color with a yellow eye, making it decidedly distinctive.

I claim:

1. A new and distinct variety of kalanchoe plant, substantially as herein shown and described, characterized particularly as to novelty by the unique combination of a very different deep reddish orange flower with a distinctive light yellowish pink eye, highly branched sturdy and upright plant habit, producing a consistent plant height ranging between about 12 and 15 inches with medium size foliage of attractive moss green to fern green color, profuse blooming habit, with substantially uniform blooming date capable of responding to short day treatment for year around blooming, ability to initiate and develop flower buds under high night temperatures of summer.

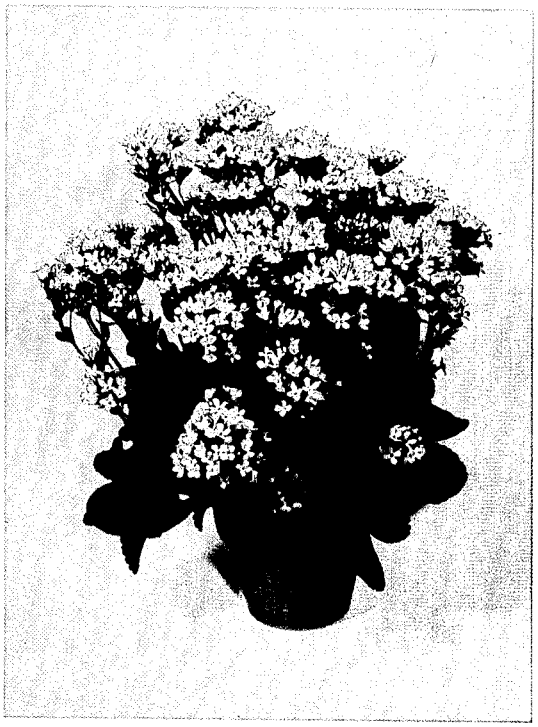
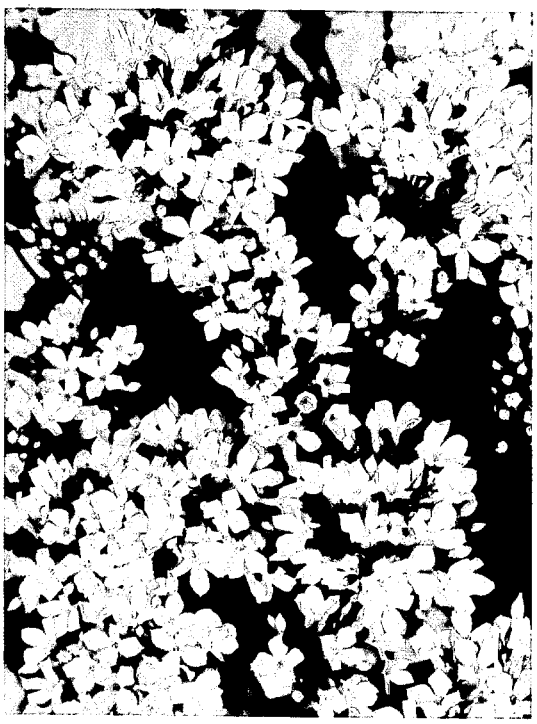

* * * * *